United States Patent
Bosser

(10) Patent No.: US 10,765,572 B2
(45) Date of Patent: Sep. 8, 2020

(54) METHOD OF ASSEMBLING AT LEAST TWO UNITS, AND A CORRESPONDING ASSEMBLED STRUCTURE

(71) Applicant: APLIX, Le Cellier (FR)

(72) Inventor: Damien Pierre Antoine Bosser, Nantes (FR)

(73) Assignee: APLIX, Le Cellier (FR)

( * ) Notice: Subject to any disclaimer, the term of this patent is extended or adjusted under 35 U.S.C. 154(b) by 580 days.

(21) Appl. No.: 15/128,024

(22) PCT Filed: Apr. 2, 2015

(86) PCT No.: PCT/FR2015/050867
§ 371 (c)(1),
(2) Date: Sep. 21, 2016

(87) PCT Pub. No.: WO2015/150709
PCT Pub. Date: Oct. 8, 2015

(65) Prior Publication Data
US 2017/0087034 A1    Mar. 30, 2017

(30) Foreign Application Priority Data
Apr. 3, 2014   (FR) ...................... 14 52957

(51) Int. Cl.
*A61F 13/62* (2006.01)
*A44B 13/00* (2006.01)
(Continued)

(52) U.S. Cl.
CPC ........ *A61F 13/625* (2013.01); *A44B 13/0047* (2013.01); *A44B 18/008* (2013.01);
(Continued)

(58) Field of Classification Search
CPC .............. A61F 13/625; A61F 13/15756; A61F 13/15699; A61F 13/62; A44B 18/008;
(Continued)

(56) References Cited

U.S. PATENT DOCUMENTS 3,935,360 A    1/1976  Brown
5,798,163 A    8/1998  Gold
(Continued)

FOREIGN PATENT DOCUMENTS

CN    1322505 A    11/2001
CN    1430708 A     7/2003
(Continued)

OTHER PUBLICATIONS

English language translation of Chinese Office Action from Chinese Application No. 2015800188757, dated Jan. 3, 2019, (8 pages).
(Continued)

*Primary Examiner* — Robert Sandy
*Assistant Examiner* — Louis A Mercado
(74) *Attorney, Agent, or Firm* — Bookoff McAndrews, PLLC

(57) ABSTRACT

A method wherein a first unit (10) is provided having a field of grip elements (12), and a second unit (20) provided with retention elements (22) suitable for co-operating with the grip elements (12) of the first unit (10) in order to provide a self-gripping fastening. The first and second units are put into contact in such a manner that the grip elements (12) of the first unit and the retention elements (22) of the second unit provide a self-gripping fastening (F). A treatment zone of the self-gripping fastening is treated in order to deform the grip elements (12) of the first unit (10) and/or the retention elements (22) of the second unit (20), whereby the first and second units (10, 20) are permanently secured to each other, thereby forming an assembled structure.

17 Claims, 7 Drawing Sheets

(51) Int. Cl.
*F16B 1/00* (2006.01)
*A61F 13/15* (2006.01)
*A44B 18/00* (2006.01)
*B32B 5/06* (2006.01)
*B32B 27/12* (2006.01)
*B32B 27/28* (2006.01)
*B32B 27/36* (2006.01)
*B32B 27/32* (2006.01)
*B32B 3/26* (2006.01)
*B32B 7/10* (2006.01)
*B32B 5/02* (2006.01)
*B32B 27/34* (2006.01)
*B32B 3/30* (2006.01)

(52) U.S. Cl.
CPC .. *A61F 13/15699* (2013.01); *A61F 13/15756* (2013.01); *B32B 3/266* (2013.01); *B32B 3/30* (2013.01); *B32B 5/022* (2013.01); *B32B 5/024* (2013.01); *B32B 5/06* (2013.01); *B32B 7/10* (2013.01); *B32B 27/12* (2013.01); *B32B 27/285* (2013.01); *B32B 27/32* (2013.01); *B32B 27/34* (2013.01); *B32B 27/36* (2013.01); *B32B 27/365* (2013.01); *F16B 1/00* (2013.01); *B32B 2262/0269* (2013.01); *B32B 2262/06* (2013.01); *B32B 2262/101* (2013.01); *B32B 2262/106* (2013.01); *F16B 2001/0028* (2013.01)

(58) Field of Classification Search
CPC ....... A44B 13/0047; B32B 5/022; B32B 3/30; B32B 5/024
See application file for complete search history.

(56) References Cited

U.S. PATENT DOCUMENTS

| | | | |
|---|---|---|---|
| 6,431,754 B1* | 8/2002 | Savicki, Sr. | A44B 19/267 156/73.1 |
| 6,701,580 B1* | 3/2004 | Bandyopadhyay | B65D 63/10 24/16 R |
| 7,018,496 B1 | 3/2006 | George et al. | |
| 7,159,921 B2* | 1/2007 | Billarant | B60R 11/00 296/210 |
| 7,185,465 B2* | 3/2007 | Pacione | A47G 27/0293 52/311.2 |
| 7,185,473 B2* | 3/2007 | Pacione | A47G 27/025 52/747.11 |
| 7,194,843 B2* | 3/2007 | Pacione | A47G 27/025 52/552 |
| 7,407,496 B2* | 8/2008 | Petersen | A61F 13/625 24/304 |
| 7,682,681 B2* | 3/2010 | Allison | B32B 3/16 428/95 |
| 8,281,463 B2* | 10/2012 | Hammer | A44B 18/0061 24/452 |
| 8,381,370 B2* | 2/2013 | Higashinaka | A44B 18/008 24/306 |
| 8,404,326 B2* | 3/2013 | Sachee | F16B 5/07 24/306 |
| 8,641,278 B2* | 2/2014 | Ducauchuis | A44B 18/0053 383/61.1 |
| 9,278,469 B2* | 3/2016 | Mahe | A44B 18/0061 |
| 9,750,312 B2* | 9/2017 | Nisogi | A44B 18/0069 |
| 2002/0002359 A1* | 1/2002 | Shingu | A61F 13/625 604/391 |
| 2003/0150087 A1 | 8/2003 | Dieterich | |

FOREIGN PATENT DOCUMENTS

| | | |
|---|---|---|
| CN | 1451063 A | 10/2003 |
| EP | 2 140 775 A1 | 1/2010 |
| EP | 2 201 857 A1 | 6/2010 |
| GB | 299825 A | 11/1928 |
| JP | S57176120 A | 10/1982 |
| JP | H0324403 A | 2/1991 |
| JP | 2002541951 A | 12/2002 |
| JP | 2003111788 A | 4/2003 |
| WO | WO 98/10728 A1 | 3/1998 |

OTHER PUBLICATIONS

Japanese Office Action from Application No. 2017-503079, dated Jan. 28, 2019, (13 pages).
International Search Report in corresponding International Application No. PCT/FR2015/050867 dated Jul. 23, 2015 (3 pages).
Chinese Office Action from Chinese Application No. 2015800188757, dated Sep. 9, 2019, (24 pages).

* cited by examiner

METHOD OF ASSEMBLING AT LEAST TWO UNITS, AND A CORRESPONDING ASSEMBLED STRUCTURE

CROSS-REFERENCE TO RELATED APPLICATIONS

This application is the U.S. national phase entry under 35 U.S.C. § 371 of International Application No. PCT/FR2015/050867, filed on Apr. 2, 2015, which claims priority to French Patent Application No. 1452957, filed on Apr. 3, 2014.

TECHNICAL FIELD

The present disclosure relates to a method of assembling a plurality of units.

BACKGROUND OF THE PRESENT DISCLOSURE

Numerous products are obtained by assembling a plurality of units, in particular a plurality of layers or sheets. This applies in particular to belts, which are generally formed by using heat to assemble together two solid and continuous bands that are separated by a layer of reinforcing cords.

Whatever the application, the various units are positioned relative to one another prior to being secured together. Several problems can then arise. The prepositioned units may be shifted unintentionally, either before or during assembly, thereby slowing down the fabrication process or fabricating a product that is defective and will need to be rejected. Worse, such an unintended shift of one or more of the units can be difficult to detect during fabrication, and might lead to danger for the user of the final product.

In order to mitigate those problems and make the positioning of the various units before and during assembly reliable, proposals have been made to use pre-assembly means such as clamps or staples. Nevertheless, such means can be difficult to remove, thereby making repositioning very difficult in the event of an error. They can also lead to localized stress zones in the product. They can also be impossible to extract, thereby leaving foreign bodies in the final product.

In certain applications, attempts have been made to use adhesive means for pre-assembly since they are less intrusive. For example, in the field of belts, it is known to apply an adhesive composition to the reinforcing cords in order to hold the two bands placed on either side of them in position.

With such means, it still remains difficult after the event to correct poor positioning of the units. Such adhesive means can be difficult to fabricate given the environmental standards and regulations that need to be complied with. They also present the drawback of easily losing their adhesive properties over time or as a consequence of poor storage conditions.

OBJECT AND SUMMARY OF THE PRESENT DISCLOSURE

One of the objects of the present disclosure is thus to provide a method enabling the above-specified drawbacks of the prior art to be remedied.

This object is achieved by a method comprising providing a first unit having a field of grip elements, in particular hooks, and a second unit provided with retention means suitable for co-operating with the grip elements of the first unit in order to provide a self-gripping fastening; putting the first and second units into contact in such a manner that the grip elements of the first unit and the retention means of the second unit provide a self-gripping fastening; and treating a treatment zone of the self-gripping fastening in order to deform the grip elements of the first unit and/or the retention means of the second unit, whereby the first and second units are permanently secured to each other, thereby forming an assembled structure.

In the method of the present disclosure, the first and second units are prepositioned prior to them being secured to each other permanently in a manner that is made reliable by means of a self-gripping fastening of the kind also referred to as a "contact closure" or a "touch fastener". The term "self-gripping fastening" should be understood herein as designating a connection that enables the first and second units to be held stationary relative to each other in at least one direction, in particular a tangential direction and/or a direction orthogonal to the junction surface between said units, which junction surface may be plane, or curved, or may present any other appropriate profile.

Under such circumstances, in particular when the self-gripping fastening holds the first and second units together stationary in a direction orthogonal to the junction surface between the two units, it can be undone only by applying a force that is considerably greater than the force applied to the two units while they are being fastened together.

A self-gripping fastening thus makes it possible, without effort, to hold at least two units together temporarily in a manner that is effective.

Where necessary, it also allows them to be separated and repositioned easily and repeatedly, while continuing to ensure that they end up being held in position at the time they are secured together permanently.

The prepositioning may also be performed without risk of damaging the units, with no external tool or attachment means being necessary.

In the present disclosure, a grip element may present any shape suitable for co-operating with complementary retention means in order to form a self-gripping closure of the above-defined type, which may be male-male, male-female, or hybrid.

A grip element may be a hook. The term "hook" should be understood herein as being an element that is suitable for hooking (in particular to a loop or a fiber), and in particular an element formed by a stem and a hook portion overlying said stem and extending laterally therefrom. Thus, an element in the form of a mushroom, a barb, a hook with one or two grip tabs, or the like, should be understood as being a hook in the meaning of the invention.

A grip element may also be in the form merely of a stem.

In conventional manner, these elements are grouped together so as to form a field. In the present application, a "field" of elements should be understood as constituting a plurality of elements, in particular at least 50 elements, and more particularly at least 200 elements, that may be distributed regularly or otherwise.

The size of the grip elements and the number of elements per unit area (density of the field of grip embodiments) may vary considerably. For example, the grip elements may present a total height measured orthogonally to the surface of the base from which they project that lies in the range 0.1 millimeters (mm) to 5 mm, and preferably in the range 0.5 mm to 1.5 mm. Preferably, the density of the field lies in the range 1 element per square centimeter ($cm^2$) to 2000 elements/$cm^2$, and preferably in the range 10 elements/$cm^2$ to 1200 elements/$cm^2$.

The retention means of the second unit may also have a wide variety of forms.

In the present application, the retention means may comprise a field of grip elements.

In another example, the retention means comprise fibers. In the present application, the term "fiber" should be understood as being an element that is fine and elongate, whether continuous or discontinuous, and in particular a fiber or a filament. The fibers may be assembled together to form a non-woven material. They may also be woven together. They may also be assembled in a bundle, thus forming a tow. The fibers may be synthetic fibers (carbon, aramid, or glass fibers) or they may be natural fibers (flax).

In an example, the second unit may thus comprise a non-woven layer of fibers that form retention means. In a variant, the second unit may also comprise a woven fabric provided with a field of loops forming retention means.

In order to secure the first and second units together permanently, the self-gripping fastening is treated in a treatment zone so as to deform those grip elements of the first unit and/or those retention means of the second unit that are situated in the treatment zone.

The self-gripping fastening may be treated in various ways, that may be considered as alternatives or that may possibly be used in combination. In non-exhaustive manner, the treatment may thus comprise applying pressure, vibration, friction, or radiation to the self-gripping fastening and/or using chemical treatment with at least one solvent and/or heat treatment, e.g. ultrasound heating (in particular generating ultrasound vibration using a sonotrode).

In an implementation, the treatment is such that after being deformed, the grip elements or the retention means form reinforcing means of the assembled structure.

In the present application, reinforcing means of a structure are means that confer on said structure a substantial portion (e.g. at least 20%, preferably at least 30%, more preferably at least 50%) of its ability to withstand at least one type of stress, in particular mechanical stress (e.g. traction strength, compression strength, or shear strength), or thermal stress, or chemical stress.

In a particular example, the treatment is such that after being deformed, the grip elements or the retention means retain a shape that is generally unchanged.

The term "generally unchanged" should be understood as being a shape that although possibly modified compared with the original shape, whether in terms of dimensions or structure, nevertheless conserves the mechanical retention properties of the element.

In this context, a fiber may possibly change diameter, length, or shape, while generally continuing to constitute retention means, in particular a fiber. A hook or a barb may have its shape and/or its dimensions modified (preferably the characteristic dimensions of the element, in particular its height, its width, and/or its thickness, vary by no more than 20%, preferably no more than 10%, still more preferably by no more than 5% relative to their initial values), while generally remaining a grip element. By way of example, on being deformed, a hook or a barb may become a stem.

In an example, when the treatment is heat treatment, the self-gripping fastening is subjected to a working temperature higher than a first melting temperature for one only of the grip elements and of the retention means.

In an example, the difference between the melting temperatures of the grip elements and of the retention means may be at least 5° C., preferably at least 10° C., or more preferably at least 20° C., for example.

It is common practice for a portion of a product to need to be reinforced, in order to improve its ability to withstand mechanical, thermal, or chemical stress. By way of example, such reinforcement may be the result of including reinforcing means in the product. The above-specified provisions of the method of the present disclosure enable a product to be reinforced by incorporating reinforcing means therein that may be in the form of fibers or of grip elements.

Because of the self-gripping fastening initially provided between the first and second units, the reinforcing means are held in position both before and during the treatment. Their proper positioning within the assembled final structure is thus ensured, thereby guaranteeing good reinforcement. When the reinforcing means are constituted by grip elements, care should be taken for example to avoid those elements being tilted or folded over during treatment, since that would be detrimental to the reinforcing effect. When the reinforcing means are constituted by fibers, care should be taken in particular to avoid the fibers moving too far away from the unit that is to be reinforced or failing to be uniformly distributed over that unit.

The method of the present disclosure may also be used for fabricating a composite element in which the retention means of one of the first and second units form reinforcing means and the retention means of the other unit form a matrix in which said reinforcing means are embedded.

In an example, the treatment zone forms a continuous line.

By way of example, it extends over a length of at least 1 centimeter (cm), and preferably at least 3 cm.

In another example, it is also possible for the treatment zone to be discontinuous, and in particular it may be formed by a set of spots.

The treatment zone preferably represents at least 50%, preferably at least 80%, in particular at least 95% of the total extent of the self-gripping fastening.

In a particularly preferred implementation, the treatment zone covers the entire self-gripping fastening. Still more preferably, it covers the entire surface area of the field of grip elements and/or of retention means.

In an example, the self-gripping fastening covers at least 50%, preferably at least 80%, and in particular at least 95% of the extent of the zone of contact between the first and second units.

In an example, the first and second units may be treated beyond the self-gripping fastening. In particular, the units may be treated in full.

The grip elements and/or the retention means may be made of a composite or polymer material that is suitable for melting at least once, in particular they may be made out of a thermoplastic material, a polymer that can be cured or post-cured.

In non-limiting manner, the grip elements and/or the retention means may thus be made out of any of the following materials: polyethylene, polypropylene or some other olefin homopolymer or copolymer such as ethylenes or alpha olefins sold under the names Affinity®, Engage®, or Exact®, or semi-crystalline polyolefins sold under the names Vistamaxx® or Versify®, or the elastomer thermoplastics sold under the names Santoprène®, Sofprene®, or Thermolast®; polyurethane of polyester, polyether, or polycarbonate type, in particular polyesters such as polyethylene terephthalate (PET), polybutylene terephthalate (PBT), polytrimethylene terephthalate (PTT), PET copolymer (PETG), poly(epsilon-caprolactone) (PCL), polylactic acid (PLA), polyester-based copolymers such as Hytrel® and Arnitel®; polyamides (PA), e.g. such as PA6, PA6.6, PA11, and PA12, polyamide-based copolymers such as Pebax® and Vestamid®, homopolymer or copolymer polyoximethylene (POM), and alloys containing at least one of the above-specified polymers.

In an example, the grip elements and/or the retention means include metal particles, generally embedded in the thermoplastic material constituting them. These metal particles make it possible, in particular during heat treatment, for the self-gripping fastening to be heated more rapidly and in more uniform manner locally, thereby improving its treatment, e.g. by induction heating.

The method of the present disclosure may also be used to assemble together more than two units. In an implementation, the method comprises providing a third unit comprising a field of grip elements suitable for co-operating with the retention means of the second unit in order to provide a self-gripping fastening; putting the second and third units into contact so that the second unit is arranged between the first and third units, and the grip elements of the third unit and the retention means of the second unit provide a second self-gripping fastening; and treating a treatment zone of the second self-gripping fastening to deform the grip elements of the third unit and/or the retention means of the second unit, whereby the second and third units are permanently secured to each other.

Preferably, the self-gripping fastenings provided between the second unit and the first and third units respectively are treated simultaneously in a single treatment step.

In a particular implementation, prior to the treatment, the grip elements of the first unit and the grip elements of the third unit are put into co-operation, the retention means of the second unit lying between said grip elements.

In an example, the units are assembled together continuously, on a production line.

Under such circumstances, and by way of example, the first and second units form respective longitudinally-extending strips, the first and second units being superposed continuously (in line) in a longitudinal direction over at least one contact zone where the grip element of the first unit and the retention means of the second unit provide a self-gripping fastening, and said self-gripping fastening is treated continuously (in line) in the longitudinal direction over at least one treatment zone. The treatment zone may be continuous or discontinuous. By way of example, the treatment may be performed by means of a wheel making continuous contact (when the treatment zone comprises at least one continuous strip), or point contact (when the treatment zone comprises a plurality of distinct zones that are spaced apart in the longitudinal direction).

The method of the present disclosure may have various applications, in particular in the field of hygiene.

In one example utilization, the method may be used for fabricating hook-carriers for diapers.

Under such circumstances, in particular, the first unit has a field of hooks and the second unit is a non-woven material, the first and second units being superposed over at least one zone of contact where the hooks of the first unit and the fibers of the second unit provide a self-gripping fastening, while preserving on opposite sides of the zone of contact both a free portion of the first unit having hooks, and also a free portion of the second unit, with the self-gripping fastening being processed so as to secure the first and second units together.

It should be observed that the term "free portion of a unit" is used to mean a portion that is not in contact with the other of the first and second portions, and that has retention means that are generally (but not necessarily) operational, i.e. suitable for co-operating with other means in order to form a self-gripping fastening.

In a second example utilization, the method of the present disclosure may be used for reinforcing a base, in particular a sheet or a composite element, by means of at least one reinforcing element of the eyelet type, at a location for a hole in said base. Under such circumstances, the reinforcing insert generally constitutes the first unit and the base generally constitutes the second unit.

The term "location for a hole" is used herein to mean a location where the base is pierced or where it is going to be pierced.

The present disclosure also provides a structure comprising at least a first layer including retention means for a self-gripping fastening and at least one second layer co-operating with the first layer over at least one assembly zone holding captive the retention means, whereby the first and second layers are permanently secured to each other.

The retention means may comprise fibers. More particularly, said layer may be constituted by a sheet of woven or non-woven fibers.

In another example, the retention means are grip elements, in particular hooks. For example, the first layer comprises a base having at least one face that has a field of grip elements projecting therefrom.

In an example, a structure of the present disclosure may be a hook-carrier for diapers. Such a hook-carrier comprises a base layer provided with a plurality of hooks and a fiber layer, generally a non-woven fiber layer, that are connected together in an assembly zone.

In yet another example, the structure of the present disclosure comprises a base and a reinforcing insert having a through bore that is fastened to a location in said base for a hole.

Generally, the bore in the insert is arranged facing the location for a hole in the base.

By way of example, the base may be a sheet, in particular a tarpaulin, e.g. constituted by a layer of non-woven material, or indeed a composite element, e.g. an internal trim panel for a vehicle.

Several implementations are described in the present disclosure. Nevertheless, unless specified to the contrary, the characteristics described with reference to any one implementation may be applied to any other implementation.

BRIEF DESCRIPTION OF THE DRAWINGS

The present disclosure can be well understood and its advantages appear better on reading the following detailed description of various implementations shown as non-limiting examples. The description refers to the accompanying drawings, in which.

DETAILED DESCRIPTION OF IMPLEMENTATIONS

Figure 1:
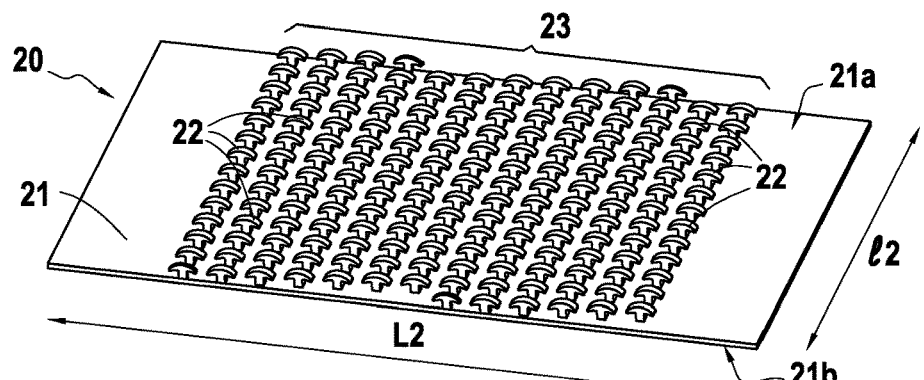
FIG. 1 is a perspective view showing two units that are to be assembled together by a first implementation of the method of the present disclosure.
Figure 1:
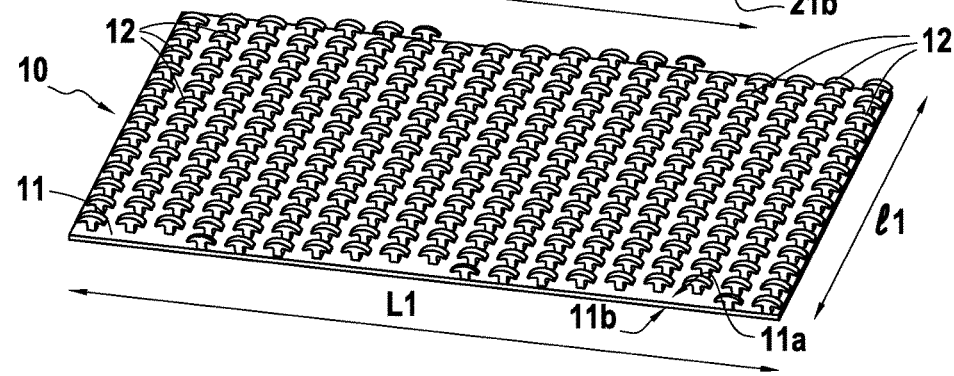
Figure 2A:
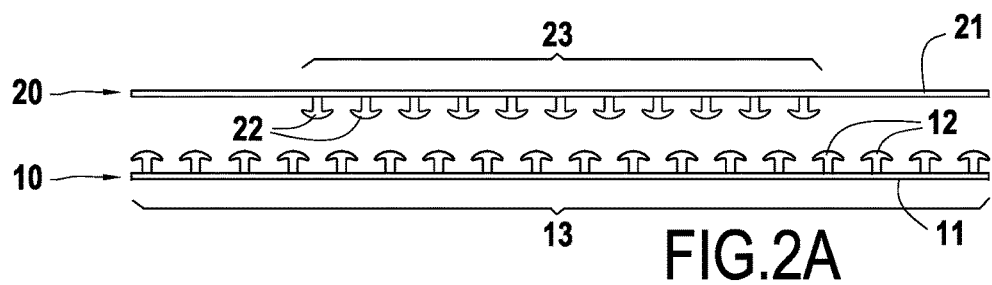
FIG. 2A is a side view of two FIG. 1 units, prior to being put into contact.
Figure 2B:
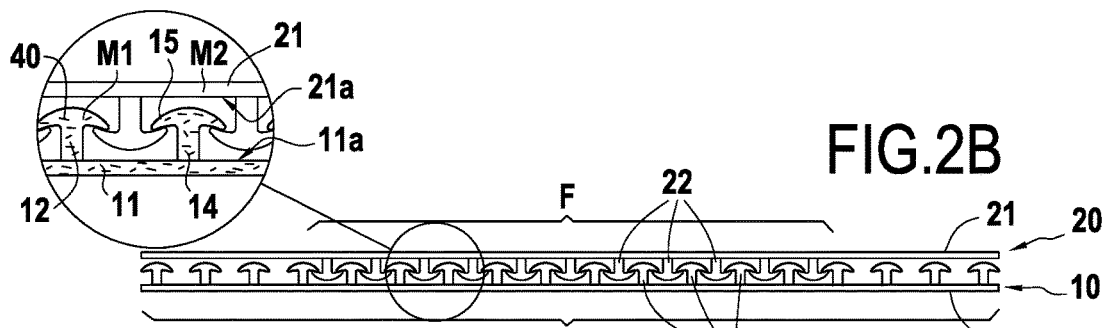
FIG. 2B is a side view of the two FIG. 1 units connected together by a self-gripping fastening.
Figure 2C:
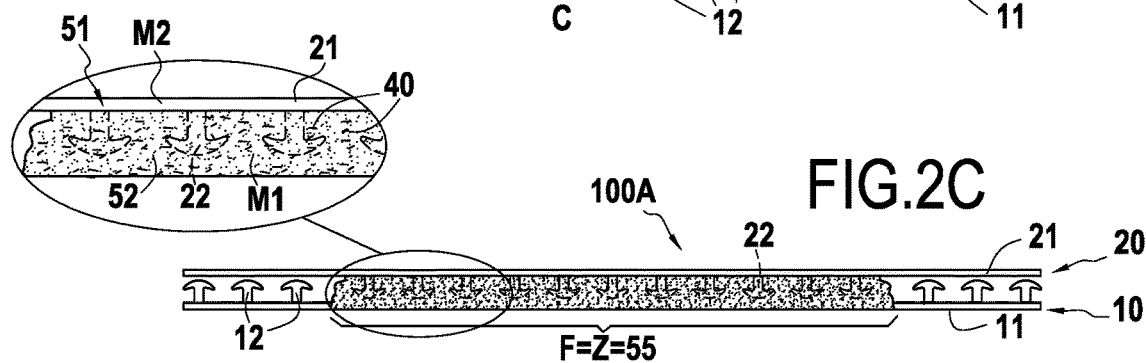
FIG. 2C is a side view of the structure that results from final assembly of the first and second units of FIG. 1.
Figure 3:
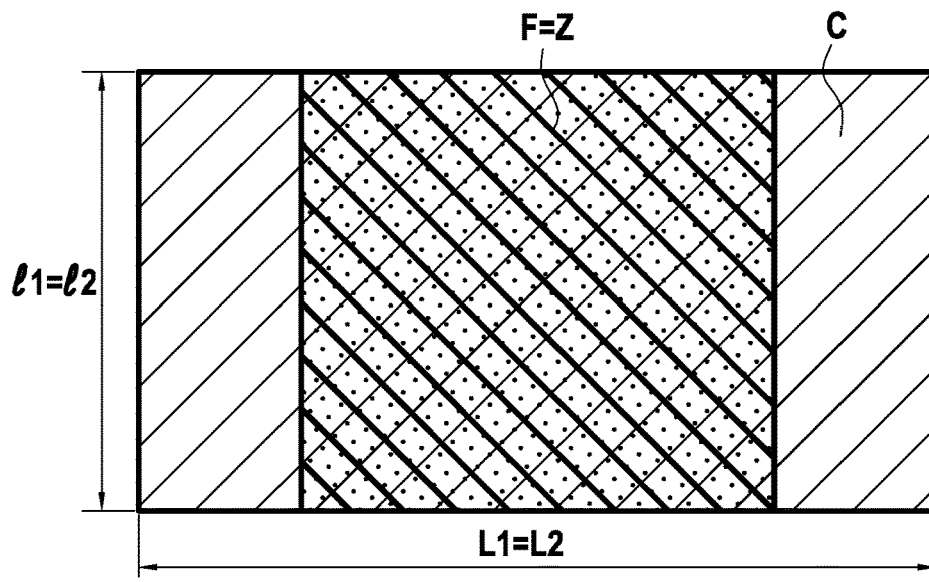
FIG. 3 is a diagram showing the treatment zone of the FIG. 2B self-gripping fastening.

FIGS. 1 to 3 show how a structure 100A (see FIG. 2C) is made by assembling together a first unit 10 and a second unit 20 in a first implementation of the method of the present disclosure.

The first unit 10 is made out of a first thermoplastic material M1 that melts at a temperature T1, in particular a curable polymer such as polyethylene for which T1 is equal to 120° C. In the particular example of FIGS. 1 to 3, the first material M1 also contains a plurality of metal particles 40 that perform a function that is described in detail below in the present disclosure.

As shown in FIG. 1, the first unit 10 comprises a base 11 defined by two main surfaces 11a and 11b, which surfaces in this example are rectangular, substantially plane, and parallel, being of length L1 and of width 11.

A plurality of grip elements 12 project from one of these main surfaces 11a (referred to below as the "junction" surface), forming a field 13 of grip elements. By way of example, the grip elements 12 may be injection molded together with the base 11. They are thus integral with the base 11, in other words forming a single piece therewith, without any interface or discontinuity, in particular at microscopic level, where they join the base 11.

In this example, the grip elements 12 are hooks, each comprising a stem 14 projecting from the junction surface in a direction that is substantially orthogonal to said surface, and a grip portion 15 that overlies said stem 14 and has two grip tabs extending laterally from the stem, on either side thereof.

In the example, the field 13 of hooks extends over the entire width 11 and the entire length L1 of the base 11. Naturally, this distribution could be very different depending on the intended application. The grip elements may cover only a portion of the surface of the first unit from which they project, e.g. at least 95%, or indeed less than 5%.

The grip elements 12 advantageously present a total height measured orthogonally to the surface 11a of the base 11 that lies in the range 0.1 mm to 5 mm, and the density of the field lies in the range 1 element/cm$^2$ to 2000 elements/cm$^2$.

The second unit 20 is made of a second thermoplastic material M2 that melts at a temperature T2 higher than T1, in particular a polymer such as a polyamide for which T2 is equal to 260° C.

The second unit 20 presents a structure that is very similar to the structure of the first unit 10, and it is therefore not described in detail below. It likewise comprises a base 21 defined by two surfaces 21a and 21b that in this example are substantially plane and rectangular, of length L2 (identical to L1 in this example) and of width l2 (identical to L1 in this example).

As shown in FIG. 1, the second unit 20 has retention means 22 adapted to co-operate with the grip elements 12 of the first unit 10.

In the example, the retention means 22 are grip elements complementary to the hooks 12, and in particular they are hooks of the same shape, forming a field 23 of hooks.

The field 23 of hooks of the second unit 20 in this example occupies only a fraction of the junction surface 21a from which it projects.

During assembly, and as shown in FIG. 2A, the first and second units 10 and 20 are positioned in such a manner that their respective junction surfaces 11a and 21a face each other.

As shown in FIG. 2B, the first and second units 10 and 20 are then brought into contact in a desired relative position.

In FIGS. 2B and 3, in particular, reference C designates the zone of contact between the first and second units 10 and 20. In this zone of contact C, the fields 13 and 23 of hooks of the first and second units 10 and 20 face each other in at least a determined zone, where they provide a self-gripping fastening referenced F resulting from co-operation between their grip elements 12 and 22.

In this state, said self-gripping fastening F holds the first and second units 10 and 20 stationary relative to each other in a direction orthogonal to their junction surfaces 11a, 21a, and also in directions tangential to those surfaces. Nevertheless, they are not held permanently, and it is easy for the two units 10 and 20 to be separated in order to be repositioned, should that be necessary.

Finally, and as shown in FIG. 2C, the self-gripping fastening F is treated in a treatment zone (referenced Z and represented by stippling in FIG. 3) corresponding in this example to the entire zone of the self-gripping fastening F, so as to secure the first and second units 10 and 20 together in permanent manner.

Figure 4A:
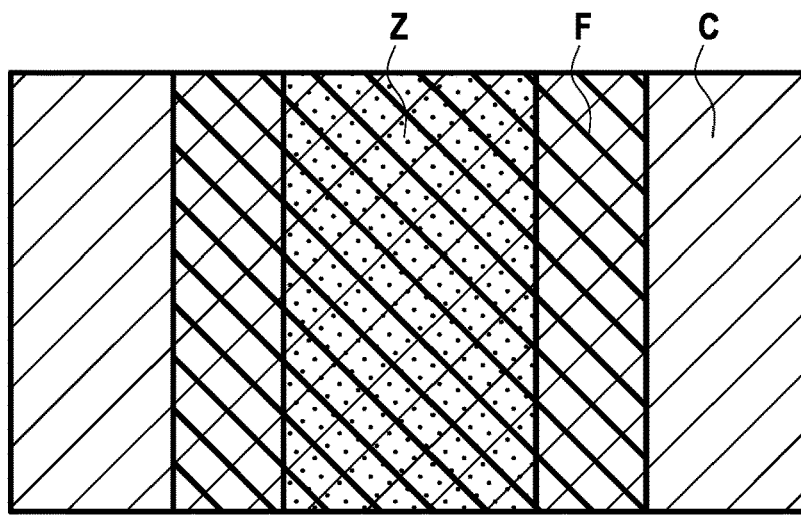
FIGS. 4A to 4C show variant distributions for the treatment of the self-gripping fastening of FIG. 2B.
Figure 4B:
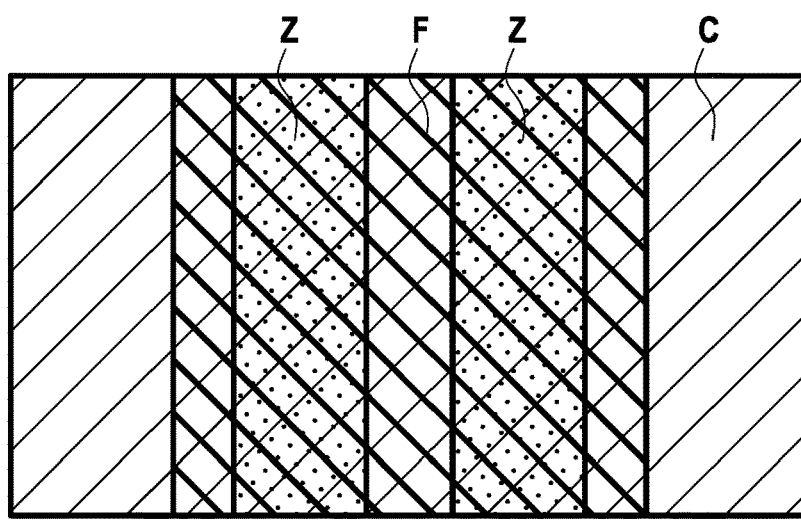
Figure 4C:
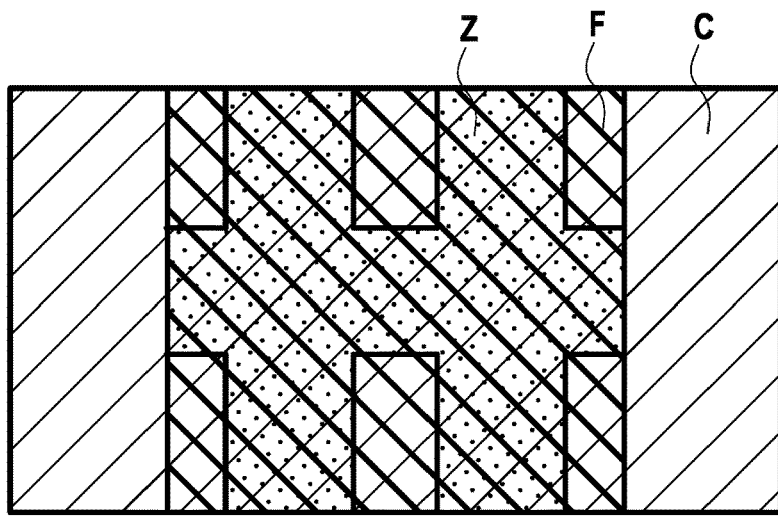

Nevertheless, this example is not limiting. In certain circumstances, the treatment zone Z may extend over a fraction only of the self-gripping fastening F. In the example of FIG. 4A, the treatment zone Z is thus in the form of a strip extending over only a fraction of the length of the self-gripping fastening F, but extending all the way across the first and second units 10 and 20 along a continuous line, extending in the width direction in this example. In the examples of FIGS. 4B and 4C, the treatment zone Z comprises a plurality of strips, extending parallel to one another or forming a grid. In other variants, the treatment zone may also be in the form of a plurality of spots or the equivalent.

In the example of FIGS. 1 to 3, the treatment zone Z is subjected to a temperature T that is higher than T1 but lower than T2, thereby causing the first unit to be deformed in said zone.

The metal particles 40, which should be understood to be optional, serve in this example to ensure that temperature increases rapidly and uniformly within the first material.

As shown in FIG. 2C, the base 11 and the hooks 12 of the first element 10 melt so as to coat the hooks 22 of the second unit 20 that have remained intact (since they do not deform).

In order to ensure that treatment is effective, avoiding deformation of the hooks 22 of the second unit, the difference between the respective melting temperatures T1 and T2 of the first and second materials M1 and M2 should be not less than 5° C., preferably not less than 10° C., and more particularly not less than 20° C.

The resulting assembled structure 100A is a one-piece block comprising a first layer 51 including the retention means for a self-gripping fastening, specifically the hooks 22, and a second layer 52 co-operating with the first layer 51 over at least one assembly zone 55 and holding captive the retention means 22, whereby the first and second layers 51 and 52 are permanently secured to each other.

The structure 100A thus forms a composite element having a matrix formed by the material of the second layer (resulting from the deformation of the first unit) and the reinforcing means are formed by the grip elements of the first layer 51, serving in particular to improve the shear and/or traction strength of the structure.

In a variant, it should be observed that the melting temperature of the first unit could equally well be higher than the melting temperature of the second unit.

Figure 5A:
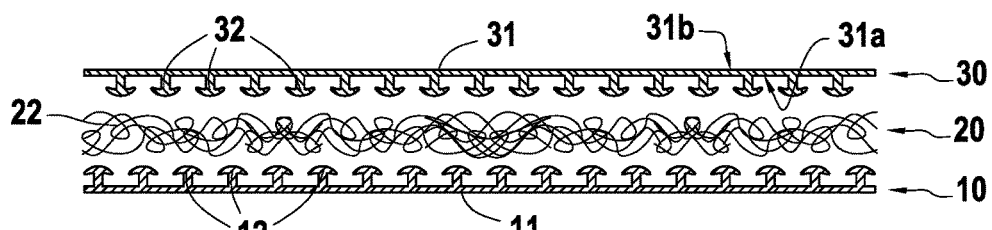
FIG. 5A is a section showing three units that are to be assembled together by a second implementation of the method of the present disclosure, the unit being shown prior to being put into contact.
Figure 5B:
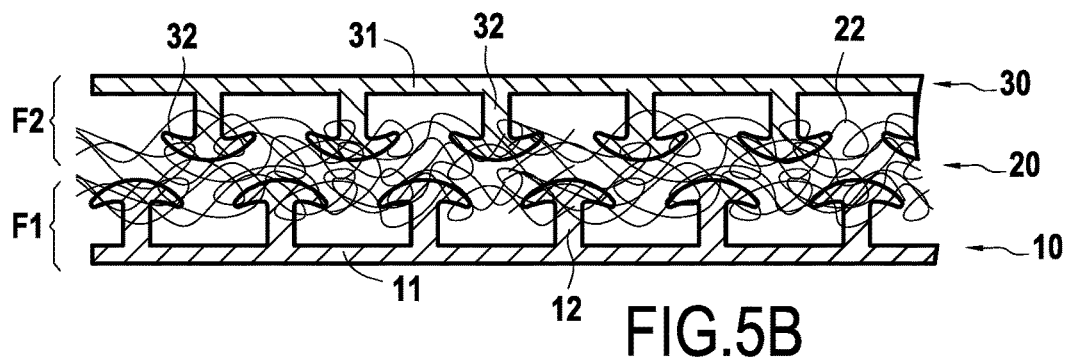
FIG. 5B is a section showing the three units of FIG. 5A connected together by a self-gripping fastening.
Figure 5C:
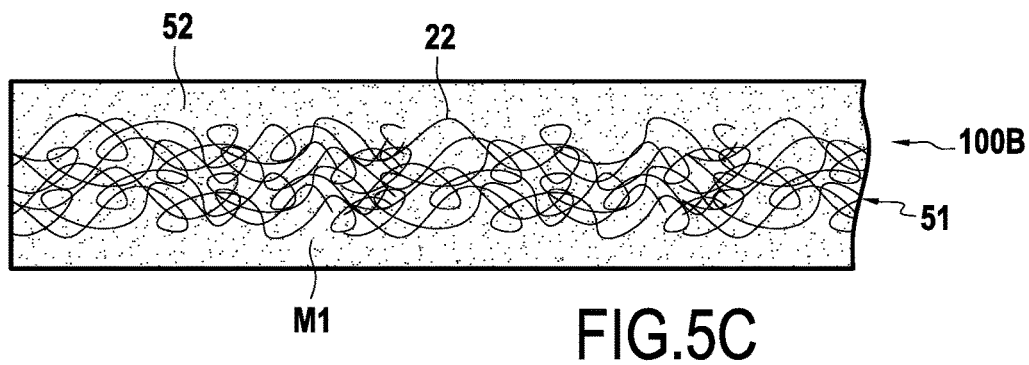
FIG. 5C is a section of the structure that results from final assembly of the three units of FIG. 5A.

FIGS. 5A to 5C show a structure 100B (see the figure) that is made by assembling together a first unit 10, a second unit 20, and a third unit 30 in a second implementation of the present disclosure.

As shown in FIG. 5A, the first unit 10 is similar to that described with reference to FIG. 1 in particular. It is therefore not described again.

In this example, the second unit 20 is constituted by a layer of non-woven material, made out of a thermoplastic material that melts at a temperature T2, higher than T1. The retention means 22 of the second unit 20, which are adapted to co-operate with the hooks 12 of the first unit 10, are formed by the tangled fibers constituting the non-woven material.

A non-woven material is made up of a plurality of fibers that are bonded together and that generally form a sheet. The fibers may be bonded together mechanically, chemically, or thermally. Three major types of non-woven material are presently known: dry-laid nonwovens (carded thermo-bonded—airlaid thermobonded—spunlace—airthrough—carded needle punched, etc.); wet-laid nonwovens; and spunmelt nonwovens (spunbond, meltblown, or a combination of both (SM, SMS, SMMS, SSMMS, . . . ), electrospun, melt-film fibrillated, solvent-spun, . . . ).

The third unit 30 is made of a meltable polymer material that, in this example, is identical to the material M1 constituting the first unit 10.

In the same manner, its structure is similar to that of the first unit 10. It thus comprises a base 31 defined by two substantially plane and parallel surfaces 31a and 31b together with a plurality of grip elements 32 adapted to co-operate with the retention means 22 of the second unit 20. In the example, these grip elements 32 form a field 33 of hooks projecting from one of the surfaces 31a of the base 31 (referred to below as the "junction" surface).

During assembly, and as shown in FIG. 5B, the first and second units 10 and 20 are put into contact in a desired position. The fibers 22 of the second unit co-operate with the hooks 12 of the first unit 10 to provide a first self-gripping fastening F1.

In the same manner, the second unit 20 and the third unit 30 are put into contact in a desired position. The fibers 22 of the second unit 20 co-operate with the hooks 12 of the third unit 30 to provide a second self-gripping fastening F2.

By means of these self-gripping fastenings F1 and F2, all three units 10, 20, and 30 are held in position relative to one another. If they are poorly positioned, they can easily be detached and then repositioned, and this can be done a large number of times without damaging them.

In the example, the three above-mentioned units 10, 20, and 30 are assembled together permanently by heat treatment, which consists in subjecting the stack to a temperature T that is lower than T2 but higher than T1.

Under the effect of heat, the first and third units 10 and 30 deform and bond together, holding captive the fibers 22 of the non-woven material, which fibers themselves remain substantially intact, with the first, second, and third units thus being permanently secured to one another.

As shown in FIG. 5C, the resulting assembled structure 100B is a composite unit comprising a first layer 51 including retention means that have been used in a self-gripping fastening, specifically the fibers 22, and a second layer 52 resulting from the deformation of the first and third units, co-operating with the first layer 51 over at least one assembly zone and holding the retention means 22 captive, whereby the first and second layers 51 and 52 are permanently secured to each other.

Figure 6:
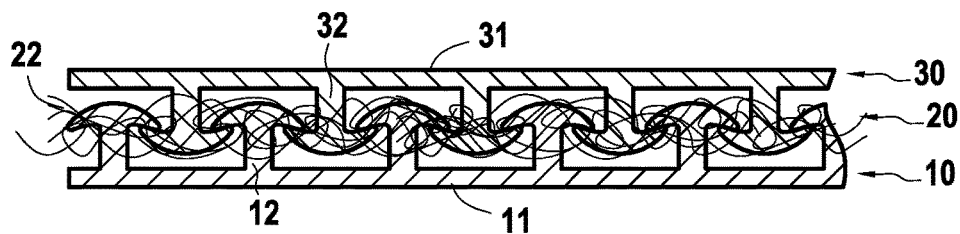
FIG. 6 shows a variant of the second implementation of the method of the present disclosure.

The fibers 22 form reinforcing means for the assembled structure 100B, serving in particular to increase its stiffness and its traction strength, and preventing the first and third units 10 and 30 from separating. In a variant implementation shown in FIG. 6, the positioning of the three units 10, 20, and 30 may be secured further in additional manner by bringing the hooks 12 of the first unit 10 and the hooks 32 of the third unit 30 into mutual co-operation prior to applying the heat treatment.

Figure 7A:
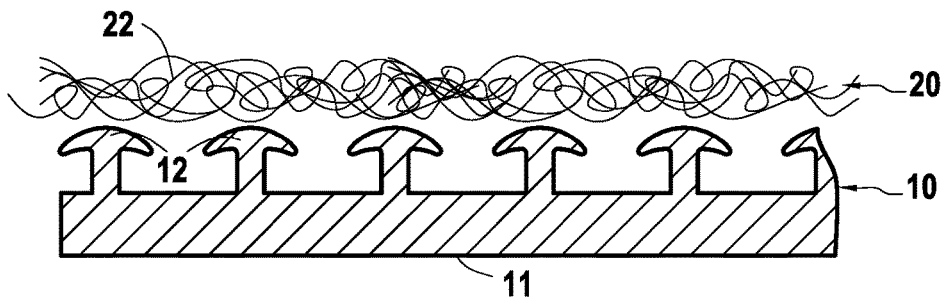
FIGS. 7A to 7C show successive steps in a third implementation of the method of the present disclosure.

As can be seen from the above, the method of the present disclosure can advantageously be used in order to form a reinforced structure. A third implementation of the method of the present disclosure illustrates such a use and is shown diagrammatically in FIGS. 7A to 7C.

In this example, a first unit 10 that is to be reinforced is made of a polymer material that melts at a temperature T1, and is substantially identical to the first unit described above with reference in particular to FIG. 1.

A second unit 20 that is formed by a layer of non-woven material constituted by tangled fibers 22 (see FIG. 7A) is put into contact with the junction surface 11a of the first unit 10 from which its grip elements 12 project, so that said fibers 22 co-operate with the hooks 12 of the first unit 10 in order to provide a self-gripping fastening F.

Figure 7B:
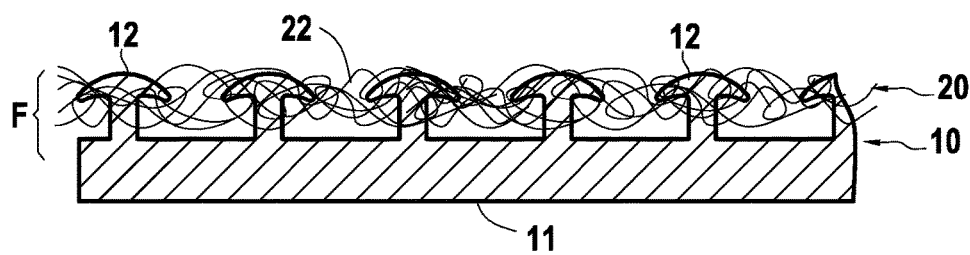

In this position, as shown in FIG. 7B, the layer of non-woven material is held stationary relative to the first unit in directions that are tangential to the junction surface 11a and in a direction orthogonal thereto.

Thereafter, the self-gripping fastening F is subjected to a temperature T that is higher than T1 but lower than T2, e.g. obtained by using a sonotrode to generate ultrasound vibration. In this position, the base 11 and the hooks 12 of the first unit melt, and they coat the fibers 22 of the non-woven material, which fibers remain substantially intact.

Figure 7C:
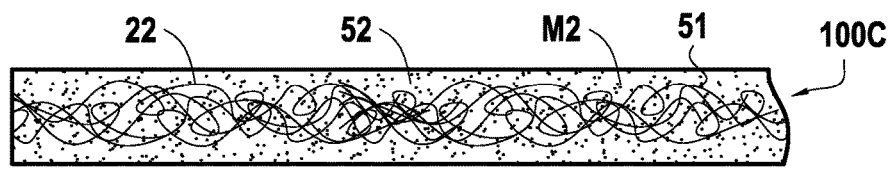

The first and second units 10 and 20 then constitute a single-piece assembled structure 100C of composite form, as shown in FIG. 7C, comprising a layer forming a matrix 52 that results from deformation of the first unit, holding captive the retention means for a self-gripping fastening, specifically the fibers 22.

Figure 8:
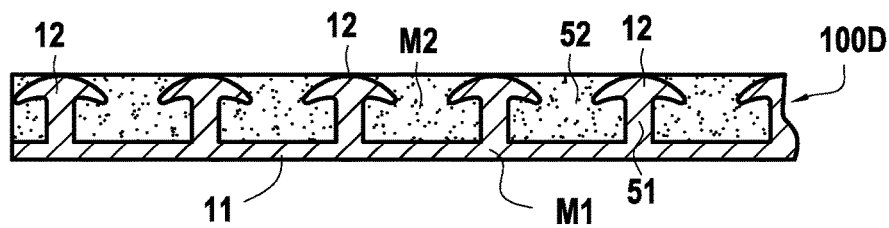
FIG. 8 shows a first variant of the third implementation of the method of the present disclosure.

In a first variant of this third implementation, shown in FIG. 8, the first unit 10 is made of a material that melts at a temperature T2 higher than the melting temperature T1 of the second unit 20.

When the self-gripping fastening F made between the two units is treated by being subjected to an intermediate temperature, higher than T1 but lower than T2, the fibers 22 melt and coat the hooks 12, that have themselves remained intact.

The first and second units 10 and 20 then constitute a single-piece structure 100D of composite form comprising a matrix (resulting from deformation of the second unit 20) reinforced by the hooks 12 of the first unit 10.

Figure 9:
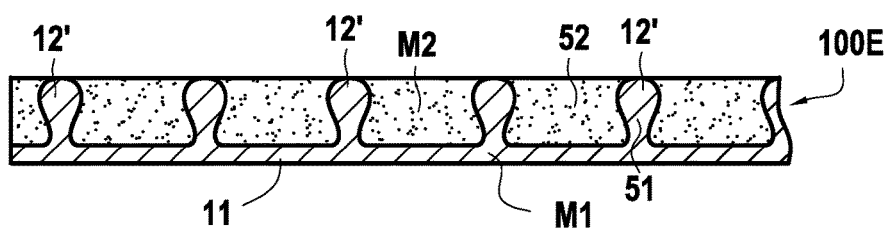
FIG. 9 shows a second variant of the third implementation of the method of the present disclosure.

In a second variant implementation shown in FIG. 9, the self-gripping fastening F is treated by being subjected to a temperature that is higher than the melting temperatures of the first and second units 10 and 20.

Under such circumstances, under the effect of high temperature, the hooks 12 melt while nevertheless retaining a generally substantially cylindrical shape.

The fibers 22 melt and serve to coat the deformed hooks 12'.

The method of the present disclosure has a wide variety of applications in numerous fields. Non-exhaustive examples are given below.

By way of example, the method of the present disclosure may advantageously be used in the field of hygiene, in particular for fabricating hook-carriers for closing diapers.

The method of the present disclosure may also be used in the automotive or aviation fields, in particular for fastening trim on doors, roof panels, or covers.

FIGS. 10, 11, 12A, and 12B show a particular application of the method of the present disclosure for fabricating hook-carriers for diapers.

Figure 10:
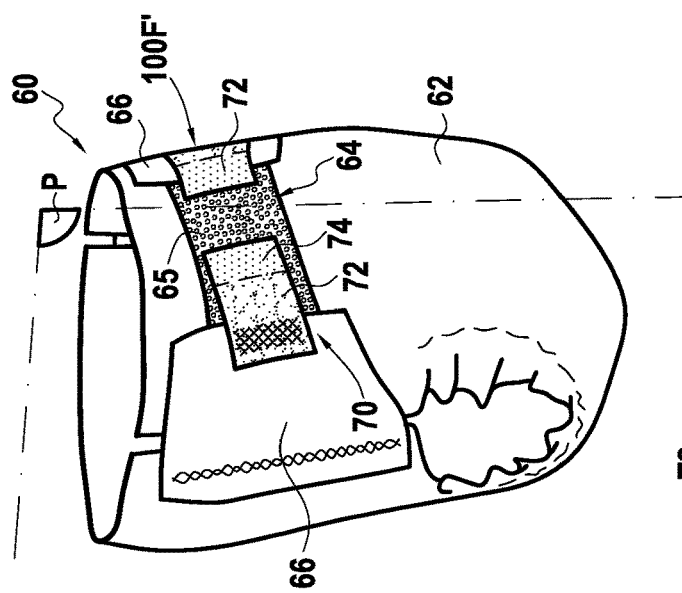
FIG. 10 is an overall view of a commonly-used diaper.

A diaper 60 of the kind shown in FIG. 10 usually comprises:
- a main or pant portion 62 having an inside face for coming into contact with the baby's skin and generally presenting an internal portion that is absorbent and an external portion that is waterproof;
- a front strip 64 centered on a plane of symmetry P of the diaper, fastened to the front of the pant portion 62 and presenting on its outside surface fibers 65, in particular loops, that are to co-operate with self-gripping hooks;
- two tabs 66, that are generally elastic, being fastened to the back of the pant portion 62 (on either side of the plane of symmetry P of the diaper 60); and
- two hook-carriers 100F' provided with self-gripping hooks that are to co-operate with the loops of the front strip in order to close the diaper 60 (as shown in FIG. 10), each hook-carrier 100F' being fastened to a respective one of the tabs 66.

As shown in FIG. 10, a hook-carrier 100F' generally comprises a support portion 72 comprising fibers (generally in a non-woven material) and that is fastened to the tabs 66 (generally by heat sealing) and a fastener portion 74 that is provided on a front face with self-gripping hooks 12 that are to co-operate with the loop-forming fibers of the front strip 64 of the diaper 60, in order to close said diaper.

In conventional manner, these two portions 10 and 20 can be assembled by attaching the rear face of a tape without hooks on a non-woven tape by means of heat sealing or adhesive. These methods present the drawback of requiring guide means for the tape that are accurate and reliable in order to ensure they are properly prepositioned prior to heat sealing or using adhesive. Furthermore, the traction strength of hook-carriers obtained in this way is sometimes insufficient, leading to the support and fastener portions unsticking or separating.

The assembly method of the present disclosure enables the above-specified problems to be solved.

Figure 11:
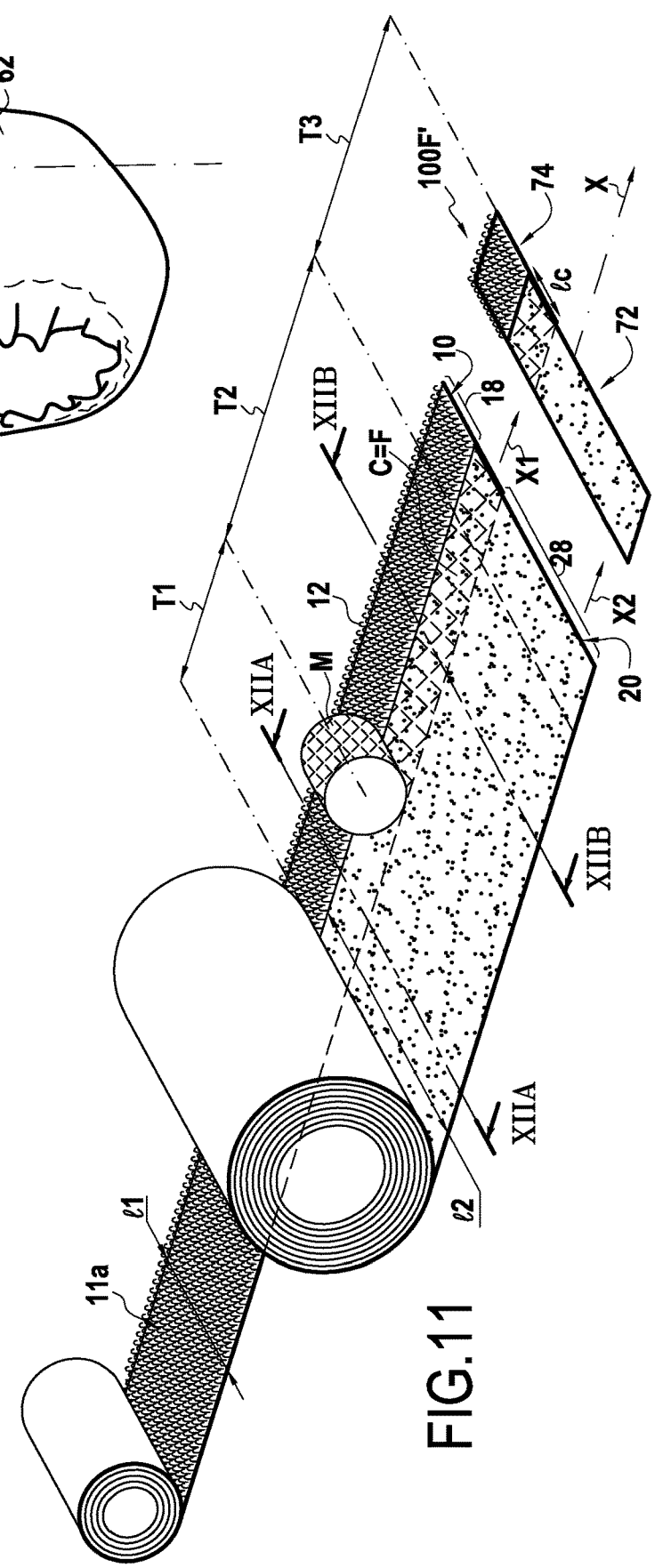
FIG. 11 shows a line for fabricating hook-carriers for diapers by implementing the method of the present disclosure.

FIG. 11 shows the method being applied on a hook-carrier fabrication line.

A first unit 10 in this example is in the form of a fastener tape of width 11 extending in a longitudinal direction X1 and having a junction face 11a covered in a field 13 of hooks, and a second unit 20 that is constituted by a support tape made of non-woven material, of width 12 and extending in a longitudinal direction X2.

In a first step represented by the segment referenced T1 in FIG. 11, the first and second tapes 10 and 20 are arranged parallel to each other and continuously superposed in a longitudinal or machine direction X over a contact zone C of width lc, the support tape 20 thus covering part of the junction face 11a of the fastener tape 10.

In the contact zone C, the hooks 12 of the fastener tape 10 and the fibers 22 of the support tape 20 provide a self-gripping fastening F. In this example the fastening F extends over all of said contact zone C.

The two tapes 10 and 20 are superposed in such a manner that a free portion 18 of the fastener tape 10 carrying the hooks 12, and a free portion 28 of the support tape 20, are preserved on either side of the contact zone C.

Figure 12A:
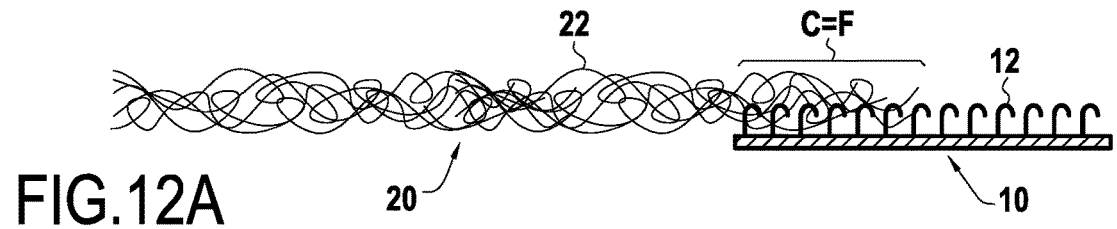
FIGS. 12A and 12B are sections respectively on XIIA-XIIA and XIIB-XIIB of FIG. 11.

FIG. 12A shows the first and second units 10 and 20 at the end of this first step. The two tapes 10 and 20 are held in position relative to each other by the self-gripping fastening F, and there is no need for additional guide and holder means.

In the second step illustrated by the segment T2, the self-gripping fastening F is treated continuously in the machine direction X.

In this example, the treatment zone Z extends over the entire zone of contact C, and the treatment is performed by means of a wheel M, in particular a heater wheel, applying pressure against the two tapes 10 and 20 in order to deform the hooks 12 of the fastener tape 10 and/or the fibers 22 of the support tape 20 in order to secure them to each other.

The treatment could also be performed without applying heat, applying only pressure, or indeed by applying only heat, in particular remotely, or indeed by any other appropriate treatment.

Depending on the materials selected to form the fastener tape 10 and the support tape 20, and depending on treatment conditions (temperature, applied pressure, etc.), the treatment may correspond to any of the examples shown and described above, in particular with reference to FIGS. 7A to 7C, 8, and 9. The characteristics described with reference to those examples are therefore not repeated here.

In order to avoid damaging hooks 12 present on the free portion 18 of the fastener tape 10, the method is nevertheless preferably performed in the manner described with reference to FIG. 8. In other words: the fastener tape 10 is made of a material that melts at a temperature T2 higher than the melting temperature T1 of the support tape 20. The self-gripping fastening F made between the two tapes 10 and 20 is treated by being subjected to an intermediate temperature that is higher than T1 but lower than T2, such that the fibers 22 melt, and coat the hooks 12 that have themselves remained intact.

Figure 12B:
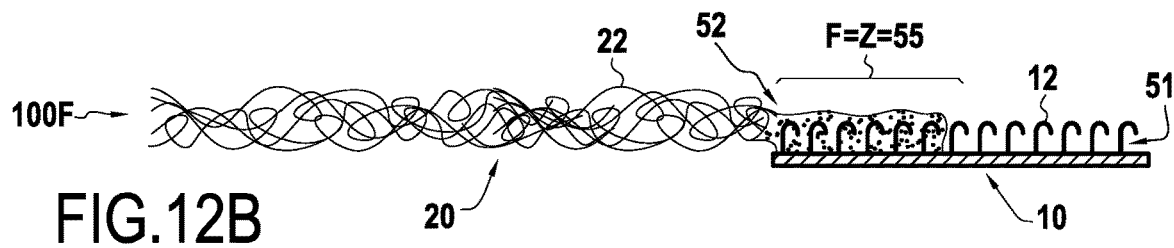

The resulting assembled structure 100F is shown in FIG. 12B. It has a first layer 51 constituted by the fastener tape 10 and comprising retention means for a self-gripping fastening (specifically the intact hooks 12 of the fastener tape 10), and a second layer 52 resulting from local deformation of the support tape 20, coating the retention means 12 over an assembly zone 55 corresponding to the treatment zone in order to hold them captive and secure said layers to each other.

In a third step illustrated by the segment T3, the assembled structure 100F is cut along a direction Y that extends substantially transversely relative to the machine direction X, thereby forming a plurality of hook-carriers 100F' for diapers.

The hook-carrier 100F' as obtained in this way is equivalent to the above-defined assembled structure 100F, of which it forms a fragment. It comprises:
- a fastener portion 74 (formed by the free portion 18 of the fastener tape 10) comprising a substantially plane base defined by two main faces, a front face and a rear face, and hooks 12 projecting from the front face of said base;
- a support portion 72 made of non-woven material (formed by the free portion 28 of the support tape) situated on the front side of the base and extending in a plane that intersects the hooks 12; and
- between the fastener portion and the support portion (in a plane intersecting both the non-woven material and the hooks), an assembly zone.

FIGS. 13 to 16 show another particular application of the method of the present disclosure for fabricating an assembled structure comprising a base, in particular a sheet or a composite material, that is reinforced in the vicinity of the location of a hole.

A sheet or tarpaulin often presents holes are to receive fastener means such as elastic straps, bungees, or the like.

Such a sheet is generally reinforced in the neighborhood of such holes by generally annular hollow reinforcing inserts of the eyelet type. Such eyelets are conventionally fastened by clip-fastening, which results in local deformation of the sheet and thus in a loss of strength.

In other applications, it is also necessary to make holes in composite elements in order to fasten them to a support, thereby running the risk of locally damaging or weakening said elements.

The assembly method of the present disclosure constitutes an advantageous solution for solving this problem.

Figure 13:
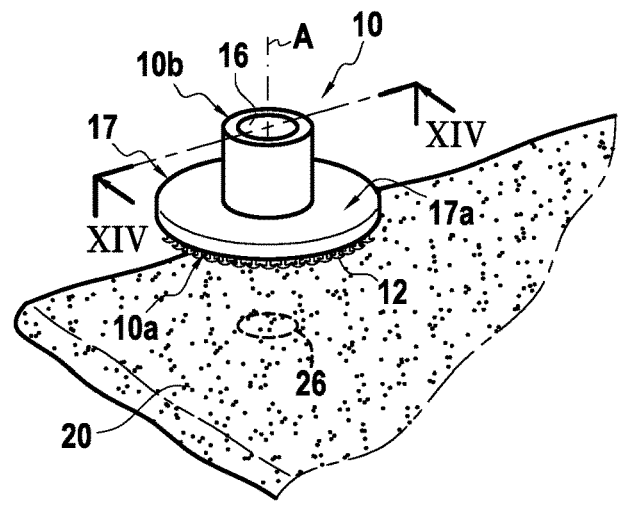
FIG. 13 shows a base that is to be reinforced locally by a reinforcing insert.

FIG. 13 shows a first unit 10 in the form of a reinforcing insert and a second unit 20 formed by a sheet of fibers, a non-woven material in this example.

The reinforcing insert 10 is for fastening to the sheet 20 at a location 26 for a hole, as shown diagrammatically in FIG. 13, in other words at a location 26 of the sheet 20 that already has a hole, or that is to have a hole made therein (which is more usual, and as described in the present example).

In the example shown, the reinforcing insert 10 is generally cylindrical in shape about a main axis A, and it defines a central through bore 16.

The reinforcing insert 10 has at least one junction surface 11a extending substantially orthogonally to the main axis A and having a field of grip elements 12 projecting therefrom and suitable for co-operating with fibers 22 of the sheet 20 in order to provide a self-gripping fastening F.

In the example of FIG. 12, the junction surface 11a is an axial end face of the insert 10.

More particular, the grip elements 12 are distributed over all of said end face 11a.

The way the reinforcing insert 10 is assembled on the sheet 20 is shown in greater detail in FIGS. 14A to 14D.

Figure 14A:
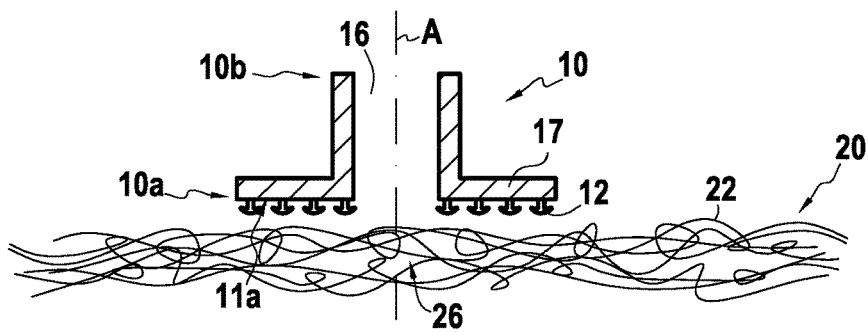
FIGS. 14A to 14D are sections on XIV of FIG. 13 showing the various steps of assembling the reinforcing insert.
Figure 14B:
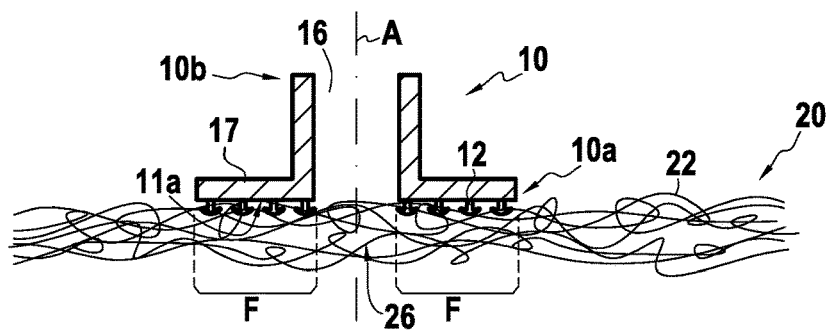

In a first step shown in FIGS. 14A and 14B, the reinforcing insert 10 is brought into contact with the sheet 20 so that the grip elements 12 that project from its junction surface 11a come to co-operate with the fibers 22 of the sheet 20 in order to make a self-gripping fastening F. The bore 16 is placed substantially in register with the location 26 for the hole.

Figure 14C:
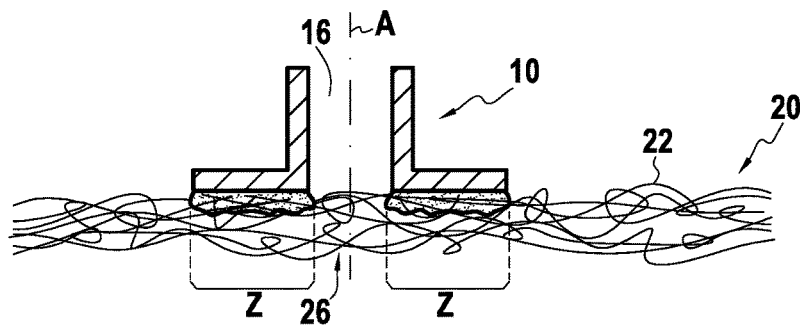

In a second step shown in FIG. 14C, the self-gripping fastening F is treated. Depending on the materials selected for forming the sheet 20 and the grip elements 12 of the reinforcing insert 10, and depending on treatment conditions (temperature, applied pressure, etc.), the treatment may correspond to any of the examples shown and described above, in particular with reference to FIGS. 7A to 7C, 8, and 9. The characteristics described with reference to those examples are therefore not repeated here.

In this example, the hooks 12 of the insert 10 melt under the effect of the treatment and coat the fibers 22 of the sheet 20 that remain substantially intact. The assembled structure 100G comprising the sheet 20 reinforced by the reinforcing insert 10 is shown in FIG. 14C. It comprises a first layer 51 constituted by the sheet 20 with retention means for a self-gripping fastening (specifically the fibers 22), and a second layer resulting from deformation of the hooks 12 of the insert 10, which coat the retention means 22 in an assembly zone 55.

Figure 14D:
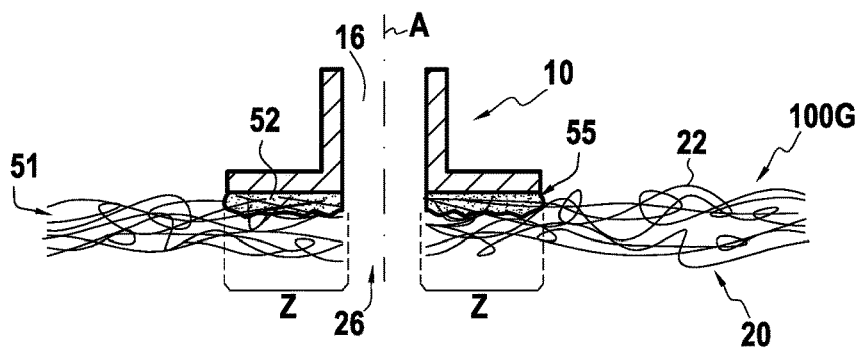

Generally, in a third step shown in FIG. 14D, the sheet 20 is then pierced at the location 26 for the hole, substantially along the main axis of the reinforcing insert 10.

The sheet 20 is thus reinforced in the neighborhood of its hole location 26 but without being damaged or deformed around the reinforcing insert 10. Furthermore, the insert 10 is fastened in reliable and permanent manner ensuring a long life for the assembly.

Nevertheless, the example shown is not limiting.

Figure 16:
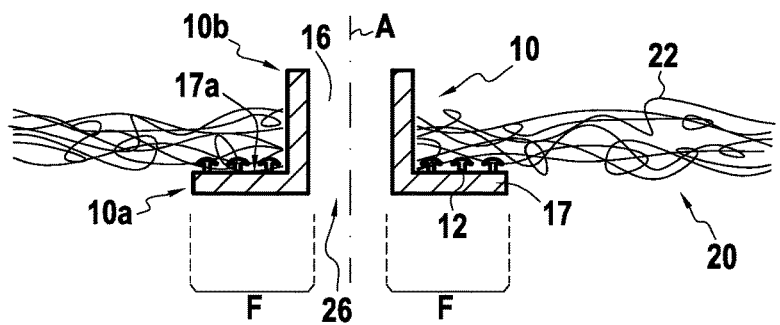
FIG. 16 shows a variant of the reinforcing method of FIGS. 13 and 14A to 14D.

In FIG. 16, the insert 10 presents an external collar 17 at one of its axial ends that is referred to as its bottom end 10a, and its junction surface carrying the gripper elements 12 is the face 17a of said collar 17 that faces towards its top end 10b.

As shown in the figure, the insert is then inserted through an orifice that has already been made in the sheet 20 so that said junction surface 17a is brought into contact with the sheet 20 in order to provide the self-gripping fastening F for securing the two units together.

The method of the present disclosure may also be used for fabricating a composite material that is reinforced by at least one reinforcing insert.

Under such circumstances, the initial steps of the method are substantially identical to those described with reference to FIGS. 13 and 14A to 14C.

Figure 15A:
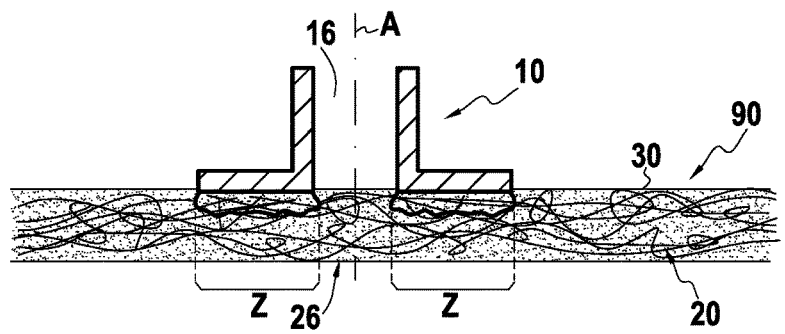
FIGS. 15A and 15B show a variant implementation of the assembly method of FIGS. 13 and 14A to 14D.

In order to form the composite element, in a step shown in FIG. 15A, the sheet 20 is associated with a third unit 30, specifically a resin. By way of example, the sheet is placed in a mold (not shown) presenting the shape that is desired or the composite element, and it is impregnated with the resin 30 inside the mold. The resin then forms the matrix of the composite, with the fibers 22 of the sheet 20 constituting its reinforcing means. The assembled structure 100H comprising the composite 90 reinforced by the reinforcing insert 10 is shown in FIG. 15A.

Figure 15B:
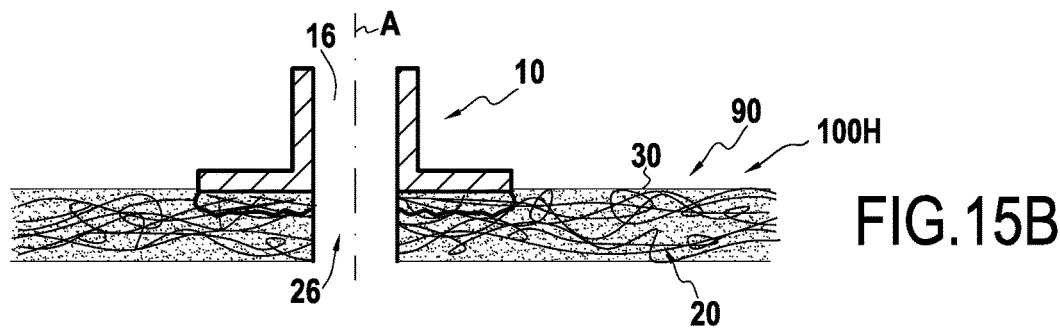

The composite 90 as obtained in this way can then be pierced through the insert without risk of damage, as shown in FIG. 15B.

In a variant, the second and third units 20 and 30 may also be assembled by performing the method of the present disclosure, in particular using the implementations described with reference to FIGS. 1 to 9.

By way of example, a composite element reinforced by at least one insert at a location for a hole may be fabricated in a manner similar to the example of FIGS. 5A to 5C, the first unit being constituted by the insert 10, the second unit being constituted by the sheet 20, and the third unit 30 comprising a base with a field of grip elements adapted to co-operate with the fibers of the sheet 20.

The first and second units form a first self-gripping fastening at the junction surface of the insert.

The second and third units form a second self-gripping fastening that preferably extends over their entire area of contact.

The first self-gripping fastening may be treated first, followed by the second, or vice versa. It is also possible for both self-gripping fastenings to be treated simultaneously.

Finally, the second and third units form a composite element in which the reinforcing means are formed by the fibers of the sheet, which have remained intact. The first unit is secured to the composite element in order to reinforce it at the location of its hole.

The invention claimed is:

1. A method comprising:
providing a first unit having a field of grip elements and a second unit provided with retention elements suitable for co-operating with the grip elements of the first unit in order to provide a self-gripping fastening;
putting the first and second units into contact in such a manner that the grip elements of the first unit and the retention elements of the second unit provide the self-gripping fastening; and
treating a treatment zone of the self-gripping fastening through a treatment in order to deform the grip elements of the first unit and/or the retention elements of the second unit, whereby the first and second units are permanently secured to each other, thereby forming an assembled structure,
wherein the treatment zone represents at least 50% of a total extent of the self-gripping fastening.

2. The method according to claim 1, wherein the treatment is such that after being deformed, the grip elements or the retention elements form reinforcing elements of the assembled structure.

3. The method according to claim 1, wherein the treatment is such that after being deformed, the grip elements or the retention elements retain a shape that is generally unchanged.

4. The method according to claim 1, wherein the treatment zone forms a continuous line.

5. The method according to claim 1, wherein the retention elements comprise fibers.

6. The method according to claim 1, wherein the grip elements and/or the retention elements are made of thermoplastic material.

7. The method according to claim 1, wherein the treatment comprises applying pressure to the self-gripping fastening.

8. The method according to claim 1, wherein the treatment comprises heat treatment.

9. The structure obtained by performing the method according to claim 1.

10. The method according to claim 1, wherein the grip elements include hooks.

11. The method according to claim 1, wherein the treatment zone represents at least 80% of a total extent of the self-gripping fastening.

12. A method comprising:
providing a first unit having a field of grip elements and a second unit provided with retention elements suitable for co-operating with the grip elements of the first unit in order to provide a self-gripping fastening;
putting the first and second units into contact in such a manner that the grip elements of the first unit and the retention elements of the second unit provide the self-gripping fastening;
treating a treatment zone of the self-gripping fastening through a treatment in order to deform the grip elements of the first unit and/or the retention elements of the second unit, whereby the first and second units are permanently secured to each other, thereby forming an assembled structure;
providing a third unit comprising a field of grip elements suitable for co-operating with the retention elements of the second unit in order to provide a self-gripping fastening;
putting the second and third units into contact so that the second unit is arranged between the first and third units, and the grip elements of the third unit and the retention elements of the second unit provide a second self-gripping fastening; and
treating a treatment zone of the second self-gripping fastening to deform the grip elements of the third unit and/or the retention elements of the second unit, whereby the second and third units are permanently secured to each other.

13. The method according to claim 12, wherein the self-gripping fastenings provided between the second unit and the first and third units respectively are treated simultaneously in a single treatment step.

14. The method according to claim 12, wherein prior to the treatment, the grip elements of the first unit and the grip elements of the third unit are put into co-operation, the retention elements of the second unit lying between said grip elements.

15. The structure obtained by performing the method according to claim 12.

16. A method comprising:
providing a first unit having a field of grip elements and a second unit provided with retention elements suitable for co-operating with the grip elements of the first unit in order to provide a self-gripping fastening;
putting the first and second units into contact in such a manner that the grip elements of the first unit and the retention elements of the second unit provide the self-gripping fastening;
treating a treatment zone of the self-gripping fastening through a treatment in order to deform the grip elements of the first unit and/or the retention elements of the second unit, whereby the first and second units are permanently secured to each other, thereby forming an assembled structure, wherein the first and second units form respective longitudinally-extending strips, the first and second units being superposed continuously in a longitudinal direction over at least one contact zone where the grip elements of the first unit and the retention elements of the second unit provide the self-gripping fastening, and said self-gripping fastening is treated continuously in the longitudinal direction over at least one treatment zone.

17. The structure obtained by performing the method according to claim 16.

* * * * *